(12) United States Patent
Lindeman (10) Patent No.: US 7,793,553 B2
(45) Date of Patent: Sep. 14, 2010

(54) SPECIMEN GRIP, HAVING A GRIP SHELL, FOR USE IN A MATERIALS TESTING MACHINE

(75) Inventor: Norman A. Lindeman, Sand Lake, NY (US)

(73) Assignee: Dynamic Systems, Inc., Poestenkill, NY (US)

( * ) Notice: Subject to any disclaimer, the term of this patent is extended or adjusted under 35 U.S.C. 154(b) by 122 days.

(21) Appl. No.: 12/313,849

(22) Filed: Nov. 25, 2008

(65) Prior Publication Data

US 2009/0139343 A1  Jun. 4, 2009

Related U.S. Application Data

(60) Provisional application No. 61/005,058, filed on Nov. 30, 2007.

(51) Int. Cl.
*G01N 3/02* (2006.01)
(52) U.S. Cl. .......................................... 73/856; 73/760
(58) Field of Classification Search ............ 73/760–860
See application file for complete search history.

(56) References Cited

U.S. PATENT DOCUMENTS

| 1,872,047 | A | | 8/1932 | Templin | |
|---|---|---|---|---|---|
| 2,350,577 | A | | 6/1944 | Vordahl | 73/51 |
| 2,634,487 | A | | 4/1953 | Rogers | 24/248 |
| 3,247,565 | A | | 4/1966 | Griffin | 24/263 |
| 3,403,549 | A | | 10/1968 | Griffin | 73/103 |
| 3,486,372 | A | | 12/1969 | Lange | 73/103 |
| 3,600,939 | A | * | 8/1971 | Steele et al. | 73/833 |
| 4,537,080 | A | * | 8/1985 | Christiansen | 73/857 |
| 5,202,542 | A | | 4/1993 | Ferguson | 219/50 |
| 5,528,942 | A | * | 6/1996 | Baratta | 73/856 |
| 5,893,876 | A | * | 4/1999 | Turkel et al. | 606/205 |
| 6,629,466 | B2 | * | 10/2003 | Grote et al. | 73/857 |
| 7,137,306 | B2 | * | 11/2006 | Ferguson et al. | 73/818 |
| 7,363,822 | B2 | * | 4/2008 | Lindeman | 73/818 |

FOREIGN PATENT DOCUMENTS

GB  617428  2/1949

\* cited by examiner

*Primary Examiner*—Max Noori
(74) *Attorney, Agent, or Firm*—Michaelson & Associates; Peter L. Michaelson (57) ABSTRACT

A specimen grip assembly which can be used with a relatively light-weight jaw in a materials testing system. The specimen grip assembly illustratively contains a grip shell and a pair of wedge-shaped specimen grips. The shell has a truncated, frusto-pyramidal exterior shape with two outwardly facing inclined surfaces, both inclined at an angle and which matingly abut and slide against complementary inclined interior surfaces of the jaw. The grips are oriented in a recess within the shell such that inclined surfaces of the grips abut against interior complementary surfaces of the shell. The shell, containing the grips and specimen, is suitably positioned within the jaw, with the shell and grips then jacked into a fixed position. The shell substantially eliminates any noticeable compliance from the specimen grips that might otherwise arise from tensile and/or compressive forces applied to the jaw and specimen grip assemblies during a test program.

22 Claims, 4 Drawing Sheets

SPECIMEN GRIP, HAVING A GRIP SHELL, FOR USE IN A MATERIALS TESTING MACHINE

CLAIM TO PRIORITY

This application claims priority of my U.S. provisional patent application entitled "Specimen Grip, having a Grip Shell, for use in a Materials Testing Machine", filed on Nov. 30, 2007 and assigned Ser. No. 61/005,058; and which is incorporated by reference herein.

BACKGROUND OF THE DISCLOSURE 1. Field of the Invention

The invention relates to apparatus for a specimen grip assembly which securely holds a test specimen in a jaw assembly of a materials testing machine. The present invention is well suited for use in a variety of different mechanical and thermo-mechanical materials testing machines, including those which provide compressive and tensile testing of a mechanical test specimen.

2. Description of the Prior Art

Conventional materials testing machines hold an end of a test specimen in proper position in a jaw during a mechanical test through any one of various mechanisms, including specimen grips, collets, or fixtures.

In such a machine, typically a known and controlled compressive and/or tensile force is applied, often under computer control and as defined by a so-called "test program", to one of two specimen grips that collectively hold opposite ends of the specimen and thus deforms the specimen under predefined test conditions. Each grip is securely held in a corresponding jaw assembly, with one such assembly being moveable while the other is fixed in position. Often, a test program may encompass applying a series of such forces—tensile and/or compressive, i.e., commonly referred to "hits", to the moveable jaw and therethrough to the specimen to increasingly deform the specimen. Dilation and/or other physical measurements are typically made of the amount of resulting deformation as or after each hit is made to the specimen. In a thermo-mechanical materials testing system, the specimen may also be controllably and self-resistively heated, such as through serial passage of electrical heating current through both the jaws and specimen, before, simultaneously with or after each such hit and as defined in the test program. Such systems are exemplified by the GLEEBLE dynamic thermo-mechanical materials testing systems presently manufactured by Dynamic Systems, Inc. of Troy, N.Y., which is the present assignee (GLEEBLE being a registered trademark of Dynamic Systems, Inc.).

One rather common method of holding a test specimen in such a materials testing machine is through use of a pair of wedge-shaped specimen grips which collectively surrounds each end of the specimen and securely fits into an appropriately shaped jaw assembly. The jaw assembly has two opposing inclined faces where each such face abuttingly and slideably mates with a complementary shaped face in a corresponding one of the pair of grips. The specimen is positioned between both grips. Thereafter, but prior to the commencement of a test program, the two specimen grips are jacked into position such that their inclined faces increasingly abut and slideably move against both faces of the jaw assembly and, through wedge-action of these mating faces, both force the grips into a highly fixed and secure position within the jaw assembly and also force the specimen grips toward each other to effectively lock the specimen in its position.

An externally generated force, typically through, e.g., a rod of a servo-controlled piston connected to the moveable jaw, is applied to that particular jaw to produce each such "hit".

Unfortunately, several drawbacks arise in a materials testing system through use of such a conventional wedge-based specimen grip and jaw assembly.

First, since the force used to deform the specimen is applied to the specimen through the moveable jaw assembly, the specimen grips and the jacking mechanism, the specimen grips must be capable of withstanding peak stresses considerably far in excess of those applied to the test specimen with minimal resulting distortion, and moreover repeatedly so during a cyclic application of such force during a test program. Some distortion, referred to as "compliance", of the jaw assembly invariably occurs. The amount of compliance that occurs is governed by the amount of force to which the jaw assembly is subjected as well as the design itself of the assembly, including its geometry and material. Disadvantageously, compliance of the jaw assembly adversely injects error into the test results for a simple reason that the compliance reduces an amount of deformation that would otherwise occur in the specimen itself resulting from each hit. Ideally, a jaw assembly, under full load, would have no compliance whatsoever, however this is generally not possible in an actual materials testing machine.

A conventional way to reduce compliance is to use relatively large and massive jaws. However, massive jaws adversely influence not only measurement of the force, but also, as more force is required to move such jaws than otherwise, reduce acceleration of, e.g., a piston rod that is used to generate the force for each hit and thus reduce its stroke rate. Reductions in the stroke rate consequently reduce a rate of deformation that can be produced in the specimen. This, in turn, concomitantly lessens an ability of the materials testing system to accurately simulate actual material working conditions that occur in, for example, certain high-speed metal production operations, such as a high-speed rolling mill, and thus, in practice, lowers the attractiveness to use such systems in such simulations. To minimize these adverse effects, the jaw assemblies should be as light-weight as possible so as not to interfere with both force measurements and acceleration produced by the piston and the ensuing rate of specimen deformation produced. However, doing so has unfortunately tended to increase compliance, thus precluding use of light-weight jaws.

Second, a conventional jaw typically has a recess which accommodates the specimen grips. Whenever a tensile force is externally applied to the jaws, the jaw exhibits compliance. Specifically as a result of the tensile force, the recess, particularly at its top edges, will tend to spread apart and distort somewhat thus diminishing the force which would otherwise hold the specimen grips together. Similarly, the vertical surfaces of the specimen grips, that would otherwise secure a proximate portion of the end of the specimen, will also exhibit compliance and tend to separate apart. This causes a loss of specimen alignment and side loading of the specimen which, in turn, may too adversely affect the accuracy of the test results. Here again, to appropriately reduce this compliance, the jaw assembly can be made of a relatively large, heavy and massive material. But, as noted above, increasing the mass of the jaw assembly adversely limits the stroke rate and hence effectively limits machine performance in accurately simulating high-speed metal production operations.

Consequently, a need exists in the art for a specimen grip assembly, preferably employing wedge-shaped specimen grips, for use in a jaw assembly of a materials testing machine, that not only exhibits substantially little, if any, noticeable compliance during the application of tensile and/or compressive forces during a succession of "hits" but also can be used in a relatively light-weight jaw.

SUMMARY OF THE INVENTION

My present invention advantageously overcomes the deficiencies in the art by providing apparatus for a specimen grip assembly that can be used with a relatively light-weight jaw and wherein the specimen grips used therein exhibit minimal, if any, noticeable compliance during an externally applied tensile and/or compressive hit including successive such hits in a "multi-hit" test program.

In accordance with my inventive teachings, the specimen grip assembly contains a grip shell and a pair of wedge-shaped specimen grips. The specimen grips are enclosed in a recess, within the grip shell, which has complementary inclined surfaces to the inclined surface of each of the specimen grips. Consequently, abutting wedge interfaces are formed between the opposing faces of the grips and the grip shell. The shell has a truncated, frusto-pyramidal exterior shape with illustratively, along its horizontal cross-section, a rectilinear shape. Both the shell and its interior space have a trapezoidal vertical cross-section. The shell has two outwardly facing inclined surfaces, both inclined at the same angle, which matingly abut and slide against complementary inclined interior surfaces of the jaw housing, effectively forming two wedge interfaces between the jaw housing and the shell. Each specimen grip also has a vertical surface at an opposing side, from its inclined surface, with a channel situated along a mid-span of the vertical surface and extending its height. The grips are oriented within the shell such that the inclined surfaces of both specimen grips face outwards toward the complementary surfaces of the shell with the vertical surfaces of the grips being adjacent to each other and their corresponding channels being both adjacent and substantially coaxial to each other. An end of the specimen is positioned within and often extends beyond a cylindrical space defined by both channels. The shell, containing the grips, is then inserted within a jaw housing. Once the shell, containing the specimen grips and specimen, is suitably positioned within the jaw housing, the shell and grips are then suitably jacked to effectively and securely lock both into position within the jaw housing.

Interposition of the shell, i.e., positioned around the specimen grips and between the jaw housing and the grips, substantially, if not totally, eliminates any noticeable compliance from occurring in the specimen grips yet allows the resulting jaw assembly to be relatively light in weight. This, in turn, permits the jaw assembly to be used in a test stand to accurately simulate certain high-speed metal forming operations that require high stroke rates which, given the compliance in the specimen grips that would otherwise result in the absence of using the shell, would not be realistic through use of just conventional specimen grip assemblies. Consequently, use of the inventive specimen grip assembly would likely and advantageously extend the utility of a materials testing system that were to employ it.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where appropriate, to designate identical or highly similar elements that are common to two or more of the figures.

DETAILED DESCRIPTION

Figure 1A:
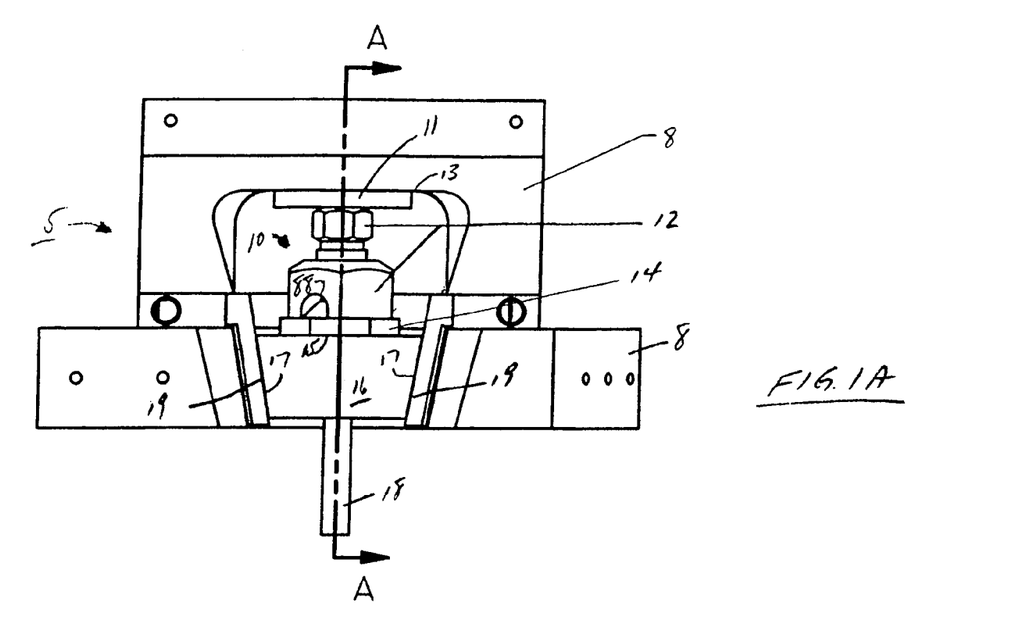
FIG. 1A depicts a side view of jaw assembly 5 used in a mechanical testing system that contains a conventional wedge-shaped specimen grip and jaw assembly.
Figure 1B:
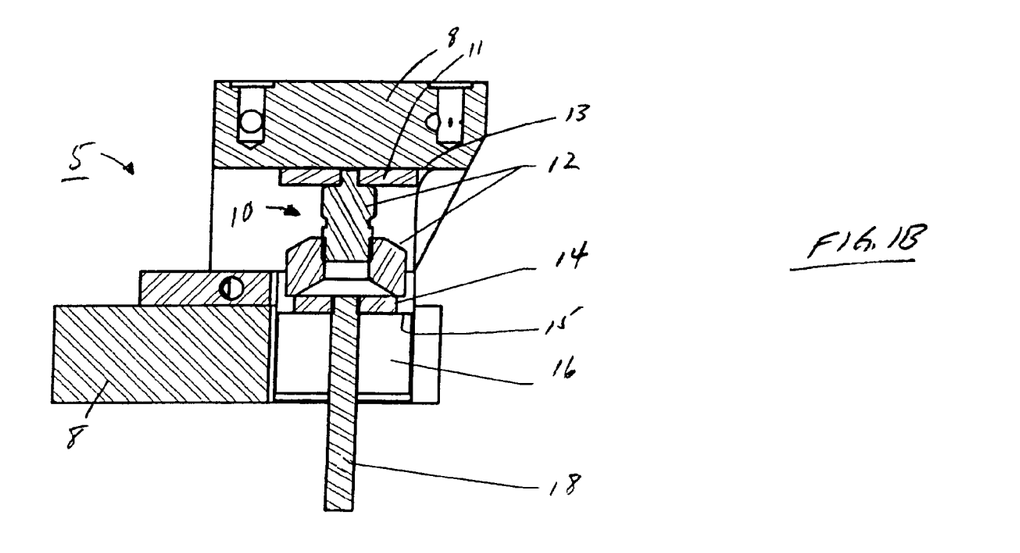
FIG. 1B depicts a cross-sectional view of jaw assembly 5 taken along lines A-A shown in FIG. 1A.

FIGS. 1A and 1B respectively depict a side view of conventional jaw assembly 5 used in a mechanical testing system and a cross-sectional view taken across lines A-A shown in FIG. 1A of this assembly.

Conventionally, as shown in these two figures, wedge-shaped specimen grips 16, which securely hold mechanical test specimen 18, are themselves positioned within two wedge surfaces 19 of jaw housing 8. Each grip has an inclined surface 17 which is complementary to and abuttingly mates with and slides against a corresponding one of wedge surfaces 19. To hold both grips firmly in place throughout each ensuing mechanical hit during a test program, jack mechanism 10, situated between upper interior surface 13 of housing 8 and upper surface 15 of specimen grip 16, is mechanically expanded to apply a continuous force between surfaces 13 and 15 which, in turn, drives grips 16 downward and, through increasing friction between complementary wedge surfaces 17 and 19, rigidly locks both grips into position in the jaw housing.

Jack assembly 10, which is conventional, relies on appropriately distending a screw within a nut (the screw and nut being collectively shown through reference numeral 12) and then mechanically locking the screw in position through adjustment of set screw 88 (or the like) located in the nut. A head of the screw pushes against spacer block 11. The external force for each hit, applied to a top surface of jaw housing 8, through typically a servo-controlled hydraulic piston rod (not shown but well-known), is transmitted through jack assembly 10 by jam nut 14 to grips 16 and ultimately to an end of the specimen.

Figure 2:
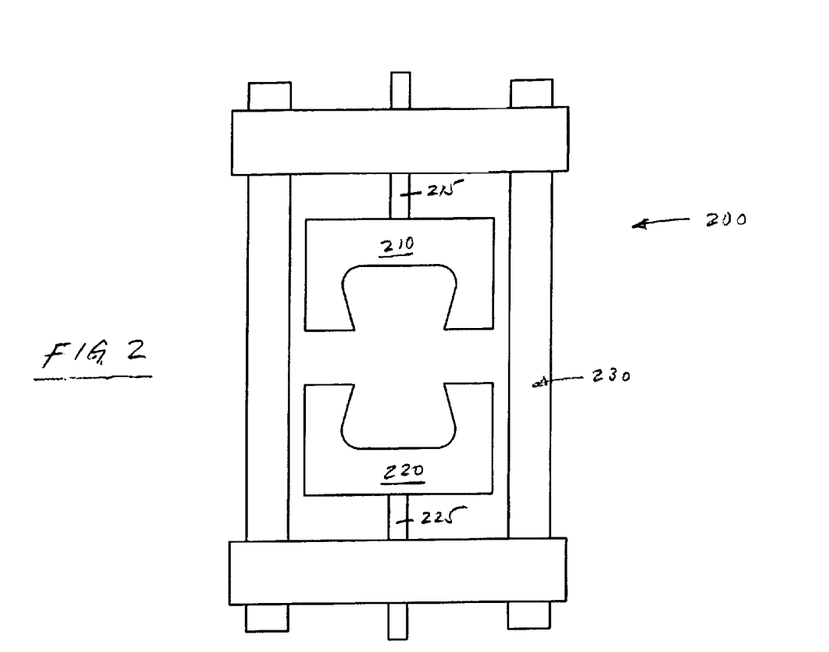
FIG. 2 depicts a simplified view of test stand 200, having two opposing jaw assemblies, as used in a conventional materials testing system.

Typically, a conventional materials testing system employs test stand 200 as shown in simplified form in FIG. 2. Such a test stand has two opposing jaw assemblies 210 and 220, shown simplified from that illustrated in FIGS. 1A and 1B. As shown in FIG. 2, one jaw assembly, e.g., assembly 220, is mounted, via shaft 225, to a solid end of test frame 230 while the other jaw assembly, e.g., assembly 210, is mounted, via shaft 215, to a test machine drive device (not shown but well-known) which may be a servo-controlled hydraulic piston, electric screw driver or other similar actuator for applying a controlled tensile or compressive force through the latter jaw assembly to the specimen itself as a hit to deform the specimen. Though not specifically shown in FIG. 2, each jaw assembly contains a pair of wedge-shaped specimen grips, each as shown in FIGS. 1A and 1B, so as to form opposing sets of specimen grips. Each set holds one end of specimen 18 (also not specifically shown in FIG. 2), with, as a result, the specimen extending between jaw assemblies 210 and 220.

As a result of, e.g., an external tensile force applied through jaw assembly 210 to the specimen, the jaw assembly and its specimen grips will unfortunately distort to some degree. Inasmuch as the jaw assembly is considerably stronger than the test specimen, the amount of distortion, or as commonly referred to "compliance", is typically rather small, though its amount is governed by the geometry of that assembly and the material from which it is fabricated. The compliance, particularly of the specimen grips, not only results in some loss of specimen alignment but also tends to inject artifacts into the test results, i.e., measured deformation, which, in turn, may slightly but adversely influence those results.

Figure 3A:
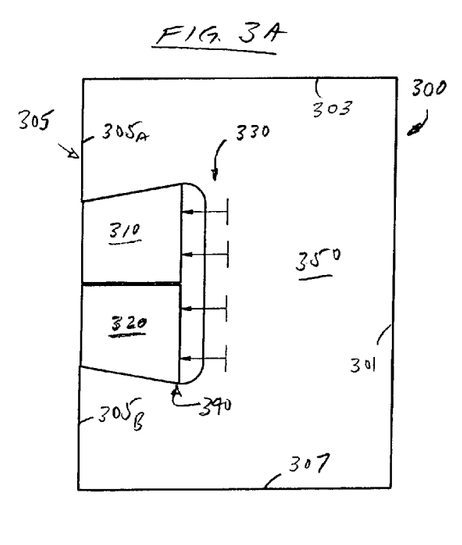
FIG. 3A depicts a simplified view of jaw assembly 300, having conventional wedge-shaped specimen grips 310 and 320, in a static unloaded state.
Figure 3B:
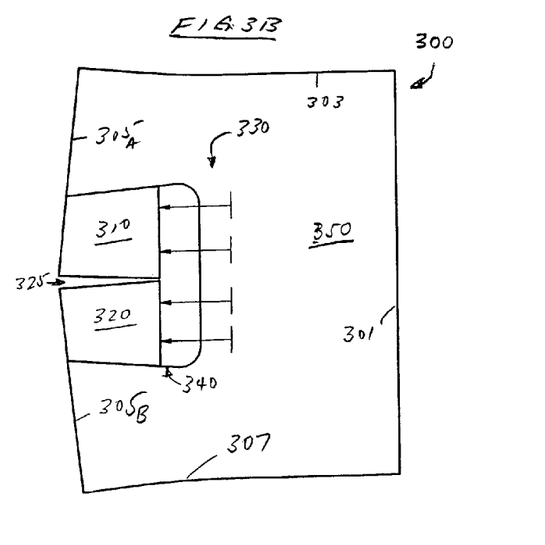
FIG. 3B depicts jaw assembly 300, shown in FIG. 3A, but in a sufficiently loaded state through application of a tensile force to the jaw as would occur during a hit, though with resulting compliance shown somewhat exaggerated for ease of illustration and understanding.

To gain an enhanced appreciation of this compliance and its adverse affects, consider FIGS. 3A and 3B.

FIG. 3A depicts a simplified view of jaw assembly 300 in a static unloaded state, i.e., without any external tensile force then being applied to the assembly. The assembly, as shown, has opposing parallel horizontal sides 303 and 307, and opposing vertical sides 301 and 305, with vertical side 305 having vertical side portions $305_A$ and $305_B$. Conventional wedge-shaped specimen grips 310 and 320 are situated within recess 340 formed in the jaw housing 350 between and behind the side portions. Once the specimen grips are jacked in place, a force in the direction shown by arrows 330 forces the inclined faces of specimen grips 310 and 320 against complementary inclined faces of the jaw housing to securely and rigidly lock both specimen grips in place in the housing. In an unloaded condition, both horizontal sides 303 and 307 remain parallel with each other, as are vertical sides 301 and 305. Side portions $305_A$ and $305_B$ remain co-planar.

However, when a sufficient tensile force is applied to jaw assembly 300 from side 301 as a result of a hit—as would be the case if this jaw assembly were the moveable jaw assembly in test stand 200 shown in FIG. 2, then, as depicted in FIG. 3B, jaw assembly 300 will distort. FIG. 3B shows the ensuing distortion (compliance) in an exaggerated fashion. As indicated, sides 303 and 307 would bulge inward, to take on a slightly convex or similar shape, while side portions $305_A$ and $305_B$ would bulge outward and cause gap 325 to appear between specimen grips 310 and 320, hence causing compliance in the grips themselves, where the test specimen is located. As a result, the specimen, rather than being rigidly secured against movement between the specimen grips, will experience movement to some degree and hence become slightly misaligned—both depending on the amount of compliance.

In line with conventional teachings in the art, such compliance could be reduced by forming jaw housing 350 from large, heavy and massive material. However, doing so will reduce a stroke rate that can be applied to jaw assembly 300 by its actuator and thus limit the rate of deformation which can be imparted to the test specimen. This, in turn, would adversely limit high-speed performance of the entire materials testing system that were to employ this jaw.

Advantageously, my inventive specimen grip assembly overcomes this deficiency in the art.

In accordance with the present invention, the specimen grip assembly contains a grip shell and a pair of wedge-shaped specimen grips. The specimen grips are enclosed in a recess, within the grip shell, which has complementary inclined surfaces to the inclined surface of each of the specimen grips. Consequently, abutting wedge interfaces are formed between the opposing faces of the grips and the grip shell. The shell has a truncated, frusto-pyramidal exterior shape with illustratively, along its horizontal cross-section, a rectilinear shape. Both the shell and its interior space have a trapezoidal vertical cross-section. The shell has two outwardly facing inclined surfaces, both inclined at the same angle, which matingly abut and slide against the complementary inclined interior surfaces of the jaw housing, effectively forming two wedge interfaces between the jaw housing and the shell. Each specimen grip also has a vertical surface at an opposing side, from its inclined surface, with a channel situated along a mid-span of the vertical surface and extending its height. The grips are oriented within the shell such that the inclined surfaces of both specimen grips face outwards toward the complementary surfaces of the shell with the vertical surfaces of the grips being adjacent to each other and the corresponding channels being both adjacent and substantially coaxial to each other. An end of the specimen is positioned within and often extends beyond a cylindrical space defined by both channels. The shell, containing the grips, is then inserted within a jaw housing. Once the shell, containing the specimen grips and specimen, is suitably positioned within the jaw housing, the shell and grips are then suitably jacked to effectively and securely lock both into position within the jaw housing.

Interposition of the shell, i.e., positioned around the specimen grips and between the jaw housing and the grips, substantially, if not totally, eliminates any noticeable compliance from occurring in the specimen grips yet allows the resulting jaw assembly to be relatively light in weight. This, in turn, permits the jaw assembly to be used in a test stand to accurately simulate certain high-speed metal forming operations that require high stroke rates which, given the compliance in the specimen grips that would otherwise result in the absence of using the shell, would not be realistic through use of conventional specimen grip assemblies. Consequently, use of the inventive specimen grip assembly would likely and advantageously extend the utility of a materials testing system that were to employ it.

Figure 4:
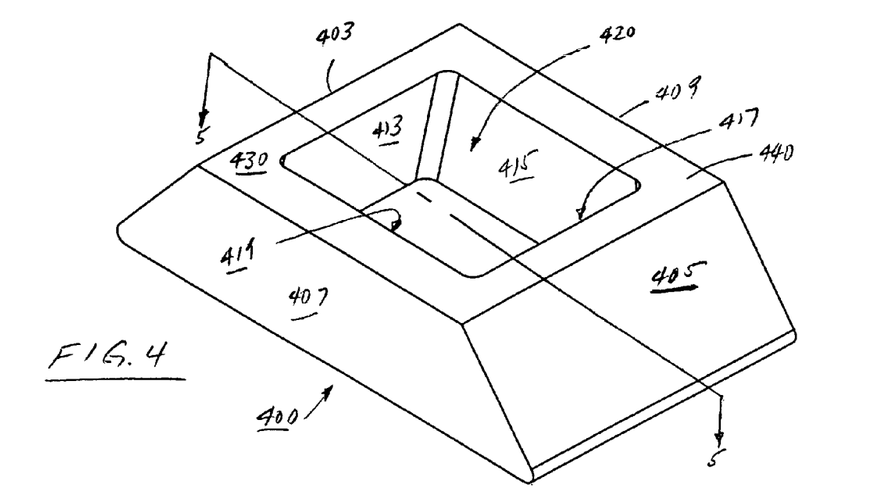
FIG. 4 depicts a top perspective view of unitary grip shell 400 as used in a first embodiment of the present invention.
Figure 5:
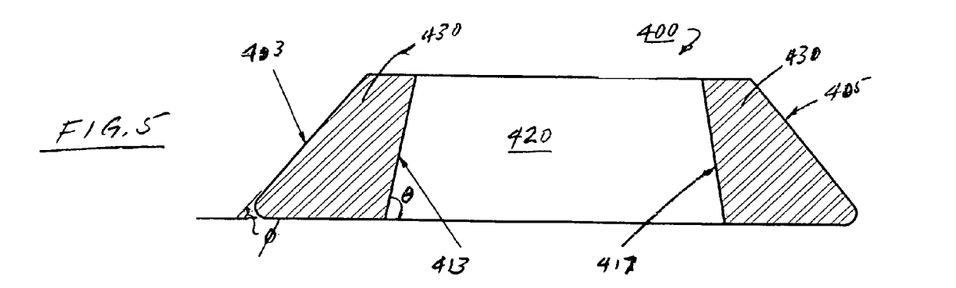
FIG. 5 depicts a cross-sectional view of grip shell 400 taken along lines 5-5 shown in FIG. 4.

With the above in mind, FIG. 4 depicts a top perspective view of unitary grip shell 400 as used in a first embodiment of the present invention and FIG. 5 depicts a cross-sectional view of grip shell 400 taken along lines 5-5 shown in FIG. 4. For enhanced understanding, the reader should simultaneously refer to these two figures throughout the following discussion of grip shell 400.

Grip shell 400 is a unitary piece of material typically formed from steel, stainless steel or other sufficiently strong material depending on physical requirements of the test stand and peak forces that are likely to occur during each "hit". For use in conjunction with the present assignee's GLEEBLE dynamic thermo-mechanical materials testing systems, grip shell 400 is preferably formed of 17-4 PH stainless steel. This material, being a martensitic, precipitation-hardened stainless steel, provides a good combination of strength, toughness and corrosion resistance.

As shown, grip shell 400 has a truncated, frusto-pyramidal exterior shape with a trapezoidal vertical cross-section and, along its horizontal cross-section, a rectilinear shape, the latter being typified by that of top surface 440. The shell has two outward-sloped surfaces 403 and 405, surface 403 being inclined at pre-defined outside angle φ with respect to a horizontal axis and surface 405 being inclined at a complementary value thereof, and two vertical surfaces 407 and 409. Recess 420 is formed by opposing interior surfaces 413 and 417, and 415 and 419. The combination of the interior and exterior surfaces defines unitary body 430. Surfaces 415 and 419 are vertically oriented, while surfaces 413 and 417, surface 413 being inclined at pre-defined inside angle θ and surface 417 being inclined at a complementary angle thereof. The angles φ and θ are not necessarily equal, though they can be, but are set to equal the angle of inclinations of abutting surfaces of the jaw housing (e.g., surfaces 19 shown in FIG. 1) and of the two specimen grips which will be inserted within recess 420, respectively. As a result of these inclined surfaces, four separate mating wedge interfaces will be formed: two opposing wedge interfaces between the jaw housing and the shell, and an separate wedge interface between the shell and each of the two specimen grips. Such a unitary shell would typically be used on a mechanical testing system that does not employ self-resistive specimen heating.

Figure 6:
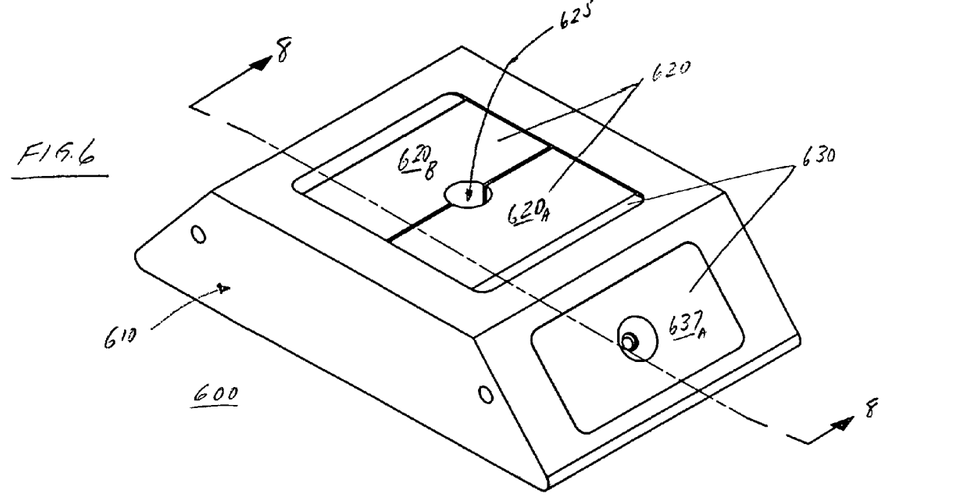
FIG. 6 depicts a top perspective view of a second embodiment of the inventive specimen grip assembly, here being assembly 600.
Figure 7:
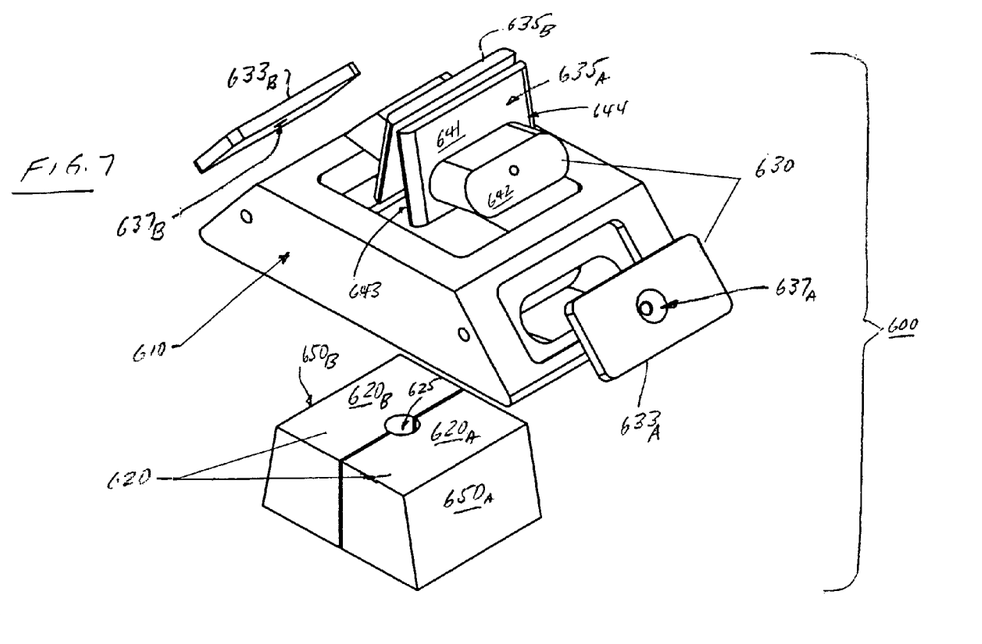
FIG. 7 depicts an exploded view of inventive specimen grip assembly 600 shown in FIG. 6, and in the same perspective view as in the latter figure, and illustrating various components that constitute inventive grip assembly 600.
Figure 8:
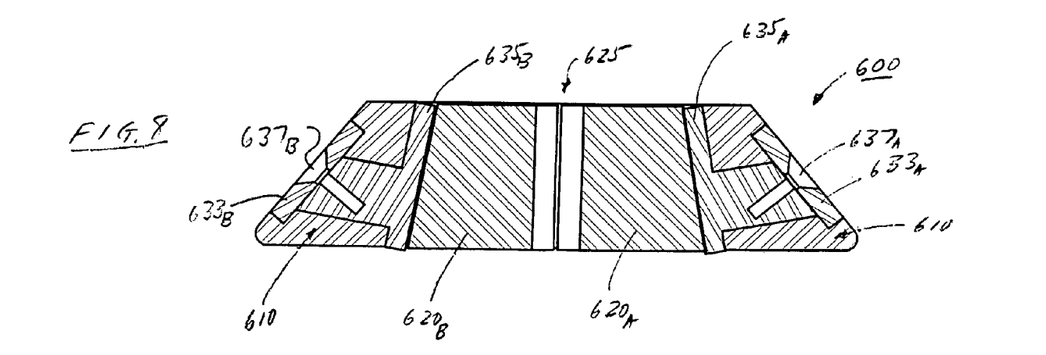
FIG. 8 depicts a cross-sectional view of inventive specimen grip 600 taken along lines 8-8 shown in FIG. 6.

Alternatively, FIG. 6 depicts a second embodiment of the inventive specimen grip assembly, here being assembly 600, that is particularly suited for use in thermo-mechanical materials testing systems, such as the GLEEBLE systems, that employ self-resistive specimen heating, i.e., where heating current serially flows through the specimen itself. FIG. 7 depicts an exploded view of inventive grip assembly 600 shown in FIG. 6, and in the same perspective view as in the latter figure, and illustrating various components that constitute inventive grip assembly 600; FIG. 8 depicts a cross-sectional view of inventive specimen grip assembly 600 taken along lines 8-8 shown in FIG. 6. For enhanced understanding, the reader should simultaneously refer to these three figures throughout the ensuing discussion.

Grip assembly 600 contains grip shell 610, inner inserts $635_A$ and $635_B$, and outer inserts $633_A$ and $633_B$. Similar to grip shell 400, grip shell 610 is also preferably formed of 17-4 PH stainless steel. With this material, inclusion of these inserts collectively provides increased thermal and electrical conductivity than would otherwise occur, hence providing increased specimen heating and cooling rates. While copper or a copper alloy is highly and sufficiently conductive, both thermally and electrically, neither has sufficient physical strength to serve as a unitary grip shell. Thus, grip shell 610 is formed of steel but employs all four inserts formed either of copper, such as CU110, or a copper alloy, such as CMW3. CMW3 is preferred inasmuch as it provides better wear resistance than pure copper. Grip assembly 600 has suitable cutouts formed in shell 610 to properly accommodate all four inserts.

Each of inserts $635_A$ and $635_B$ is itself preferably of unitary construction. Since both of these inserts are identical, I will just focus on insert $635_A$. This particular insert contains plate-like portion 641 and oval cylindrical section 642 protruding from a back surface of the former. Portion 641 has outer surface 643 which, when mounted within grip shell 610, is inclined at an angle complementary to the angle, θ (as shown in FIG. 4), of an outer inclined mating surface of the specimen grip, here specifically being surface $650_A$ of grip $620_A$, such that a tight wedge-based abutting mechanical connection can be made therebetween. Portion 641 also has inner surface 644 which, when this insert is mounted within grip shell 610, is also inclined at an angle complementary to angle θ of an inner inclined surface of the grip shell so that a similarly tight, wedge-based abutting mechanical connection can be made between the shell and this insert.

Prior to operation, the shell is illustratively assembled by first appropriately situating an end of the specimen between opposing specimen grips 620, formed of individual grips $620_A$ and $620_B$, and in cylindrical space 625 formed therebetween. Inserts $635_A$ and $635_B$ are then positioned within grip shell 610 with their cylindrical ends extending through corresponding cutouts. Thereafter, specimen grips 620 are positioned between inserts $635_A$ and $635_B$ such that outwardly located inclined surfaces $650_A$ and $650_B$ of specimen grips 620 slide along and abutting mate with these two inserts. Thereafter, inserts $633_A$ and $633_B$ are fastened, through suitable screws inserted through holes $637_A$ and $637_B$, to inserts $635_A$ and $635_B$. Each of inserts $633_A$ and $633_B$ specifically provides an appropriate mechanical contact surface to mate with a corresponding inclined surface of the jaw housing. Inserts $633_A$ and $635_A$, when installed, form insert pair 630. Next, the shell is appropriately placed into the jaw assembly and then jacked 10 into a secured, fixed position.

The inclined surfaces of the jaw housing contact with the inclined surfaces of the assembled grip shell and provide thermal and electrical conductivity as well as the mechanical support. Advantageously, the four inserts in grip shell 610 provide lower resistance electrical and thermal paths from the jaw assembly to specimen grips 620 than would otherwise arise if the shell were to be formed solely of steel (as is the case with shell 400 shown in FIG. 4). The current path, for one direction of current flow, is from the jaw housing through the inserts and into specimen grips 620 (the opposite occurring for reverse current flow). The four inserts also serve to properly and effectively cool the specimen grips 620 by extracting heat from these grips and then transmitting the extracted heat to the jaw housing which is typically water cooled.

Moreover, when the grip shell is used, a resulting jaw assembly can be made of a lighter and lower strength material than previously practiced in the art in order to obtain similar levels of compliance levels that would result in a much larger and heavier jaw. Doing so advantageously reduces cost of the jaw assembly.

Though space 625 is illustratively shown as being cylindrical with a circular cross-section, hence with each channel formed in the adjacent vertical surfaces of specimen grips $620_A$ and $620_B$ having a semi-circular cross-section, each of these channels could alternatively have a cross-sectional shape that is square, rectangular, triangular or of another appropriate shape such that space 625 will properly accommodate, and, when the specimen grips are suitably jacked, abuttingly encircle and tightly secure a corresponding complementary-shaped end portion of the specimen.

Additionally, while inner opposing inclined surfaces 413 and 417 (see FIGS. 4 and 5) of grip shell 400 and corresponding inclined surfaces of grip shell 610 can be inclined at the same angle, they need not be.

Moreover, the angles at which each of surfaces $650_A$ and $650_B$ of specimen grips $620_A$ and $620_B$, respectively, is inclined need not be exactly complementary to that of a corresponding one the inner opposing inclined surfaces of grip shell 610. Inasmuch as one of plate-like inserts $635_A$ and $635_B$ is situated between each specimen grip and grip shell 610, then small angular differences between the latter two can be accommodated by appropriately designing the inclination of the surfaces of the plate-like inner insert, such as surfaces 643 and 644 of insert $635_A$, accordingly. Doing so will still yield abutting wedge-like interfaces between each of the specimen grips and its adjacent insert, and each such insert and the grip shell that should still be sufficient to frictionally lock, by jacking, the entire specimen grip assembly in place within the jaw housing.

While each insert pair, such as insert pair 630, is shown as being formed of separate inner and outer inserts (correspondingly inner insert 635$_A$ and outer insert 633$_A$ for insert pair 630), the insert pair could instead be reshaped appropriately and formed as a single, unitary insert, in which case, once that insert is installed within grip shell 610, cylindrical section 642 would be flush with one of the outer inclined surfaces of grip shell 610, and thus provide a contact surface for the jaw housing and eliminate a need to use outer insert 633$_A$.

Further, though each of grip shells 400 and 610 has been shown and described as having a horizontal cross-section that is rectilinearly shaped, that cross-sectional shape could instead be square, triangular, circular or another appropriate shape as dictated by the geometry and other pertinent characteristics of the jaw housing and specimen grips as long as a suitable wedge-shaped interface is formed between the grip shell and each of the specimen grips and, if the above-described inserts are used, also between each of the former and a corresponding surface of each of the inner inserts.

Lastly, grip shells 400 and 610, as shown and described, are each preferably formed as a unitary piece of material, though shell 610 has suitable cutouts to accommodate both the inner and outer inserts. Alternatively, each of these grip shells could be fabricated of individual, discrete component parts that are appropriately fastened together in a conventional manner. The resulting grip shell must still be able to appropriately withstand a sufficiently high tensile or compressive force that is expected to occur during each hit but without exhibiting noticeable compliance in either itself or permitting it to occur in the specimen grips.

Although various preferred embodiments, each of which incorporates the teachings of the present invention, have been shown and described in detail herein, those skilled in the art can readily devise many other embodiments that still incorporate these teachings.

I claim:

1. A specimen grip assembly for use in a materials testing machine comprising:
   first and second specimen grips for securely holding an end portion of a test specimen therebetween, the first and second grips respectively having first and second outwardly located surfaces, each of the first and second surfaces being inclined at a first predefined angle; and
   a grip shell having first and second internal inclined surfaces, each of the first and second internal inclined surfaces of the grip shell being inclined at a predefined angle complementary to the first predefined angle at which the first and second surfaces, respectively, of the specimen grips are inclined, the grip shell being positioned around the specimen grips such that the first and second surfaces of the specimen grips abuttingly mate with and slide against the first and second inclined surfaces, respectively, of the grip shell so as to define a wedge-like interface between each specimen grip and the grip shell;
   wherein, once the specimen grip assembly is fixedly secured within a jaw of the testing machine, a subsequent tensile or compressive force applied through the jaw and the grip assembly and sufficient to deform the test specimen will not generate any appreciable and noticeable compliance in the first and second specimen grips.

2. The specimen grip assembly recited in claim 1 wherein the grip shell is a unitary piece of material.

3. The specimen grip assembly recited in claim 2 wherein the grip shell has a truncated frusto-pyramidal exterior shape with a vertical cross-sectional shape that is trapezoidal.

4. The specimen grip assembly recited in claim 3 wherein the grip shell has a horizontal cross-sectional shape that is rectilinear.

5. The specimen grip assembly recited in claim 3 wherein the grip shell further comprises:
   first and second external sloping surfaces at opposing ends of the grip shell, each of sloping surfaces being inclined at a predefined second angle so as to abuttingly mate with and slide against a complementary shaped surface of a jaw housing such that a separate wedge-shaped interface is formed between the jaw housing and each end of the grip shell.

6. Apparatus for a jaw assembly for use in a materials testing machine comprising:
   a jaw housing;
   a specimen grip assembly situated within the jaw housing and having:
      first and second specimen grips for securely holding an end portion of a test specimen therebetween, the first and second grips respectively having first and second outwardly located surfaces, each of the first and second surfaces being inclined at a first predefined angle; and
      a grip shell having first and second internal inclined surfaces, each of the first and second internal inclined surfaces of the grip shell being inclined at a predefined angle complementary to the first predefined angle at which the first and second surfaces, respectively, of the specimen grips are inclined, the grip shell being positioned around the specimen grips such that the first and second surfaces of the specimen grips abuttingly mate with and slide against the first and second inclined surfaces, respectively, of the grip shell so as to define a wedge-like interface between each specimen grip and the grip shell;
   a jacking mechanism, situated within a recess in the jaw housing, for applying a mechanical force between an interior surface of the jaw housing and a surface of the specimen grip assembly so as to fixedly secure the specimen grip assembly into position within the jaw housing;
   wherein, once jacking mechanism is set to apply the force between the jaw housing and the specimen grip assembly, a subsequent tensile or compressive force applied through the jaw housing and the grip assembly and sufficient to deform the test specimen will not generate any appreciable and noticeable compliance in the first and second specimen grips.

7. The apparatus recited in claim 6 wherein the grip shell is a unitary piece of material.

8. The apparatus recited in claim 7 wherein the grip shell has a truncated frusto-pyramidal exterior shape with a vertical cross-sectional shape that is trapezoidal.

9. The apparatus recited in claim 8 wherein the grip shell has a horizontal cross-sectional shape that is rectilinear.

10. The apparatus recited in claim 8 wherein the grip shell further comprises:
    first and second external sloping surfaces at opposing ends of the grip shell; and
    the jaw housing has first and second internal surfaces that are inclined at an angle complementary to the first and second external sloping surfaces, respectively, of the grip shell;
    the first and second external sloping surfaces of the grip shell abuttingly mating with and sliding against the first and second internal inclined surfaces of the jaw housing such that a separate wedge-shaped interface is formed between the jaw housing and each end of the grip shell.

11. A specimen grip assembly for use in a materials testing machine comprising:

first and second specimen grips for securely holding an end portion of a test specimen therebetween, the first and second grips respectively having first and second outwardly located surfaces, each of the first and second surfaces being inclined at a first predefined angle;

a grip shell having first and second internal inclined surfaces and positioned around the specimen grips; and first and second inserts located within the grip shell, both of the inserts being more conductive, thermally and electrically, than the grip shell itself is, wherein each of the inserts has an outer surface inclined at an angle complementary to the first predefined angle and both inserts are partially situated between the first and second inclined outer surfaces of the first and second specimen grips and the first and second internal surfaces of the grip shell, respectively, so as to abutting engage with the first and second specimen grips, respectively, and define a separate wedge-like interface between each of the specimen grips and the first and second inserts and, to each provide corresponding external contact surfaces for the grip shell; and wherein, once the specimen grip assembly is fixedly secured within a jaw of the testing machine, a subsequent tensile or compressive force applied through the jaw and the grip assembly and sufficient to deform the test specimen will not generate any appreciable and noticeable compliance in the first and second specimen grips.

12. The specimen grip assembly recited in claim 11 wherein the grip shell is a unitary piece of material.

13. The specimen grip assembly recited in claim 12 wherein the grip shell has a truncated frusto-pyramidal exterior shape with a vertical cross-sectional shape that is trapezoidal.

14. The specimen grip assembly recited in claim 13 wherein the grip shell has a horizontal cross-sectional shape that is rectilinear.

15. The specimen grip assembly recited in claim 13 wherein the grip shell further comprises:

first and second external sloping surfaces at opposing ends of the grip shell; and the jaw housing has first and second internal surfaces that are inclined at an angle complementary to the first and second external sloping surfaces, respectively, of the grip shell;

the first and second external sloping surfaces of the grip shell abuttingly mating with and sliding against the first and second internal inclined surfaces of the jaw housing such that a separate wedge-shaped interface is formed between the jaw housing and each end of the grip shell.

16. The specimen grip assembly in claim 13 wherein the first and second inserts comprise first and second inner inserts and first and second outer inserts, respectively, wherein:

the first and second inner inserts extend between the first and second surfaces of the first and second specimen grips and the first and second inclined surfaces of the grip shell, respectively, and abuttingly engage with the first and second specimen grips, respectively, so as to form a wedge-like interface between one of the specimen grips and a corresponding one of the inner inserts; and the first and second outer inserts extend between the first and second inner inserts and the first and second external surfaces of the grip shell so as to abuttingly engage with the first and second inner inserts, respectively, and each one of the outer inserts provides the corresponding external contact surface for the grip shell.

17. Apparatus for a jaw assembly for use in a materials testing machine comprising:

a jaw housing;

a specimen grip assembly situated within the jaw housing and having:

first and second specimen grips for securely holding an end portion of a test specimen therebetween, the first and second grips respectively having first and second outwardly located surfaces, each of the first and second surfaces being inclined at a first predefined angle;

a grip shell having first and second internal inclined surfaces and positioned around the specimen grips; and first and second inserts located within the grip shell, both of the inserts being more conductive, thermally and electrically, than the grip shell itself is, wherein each of the inserts has an outer surface inclined at an angle complementary to the first predefined angle and both inserts are partially situated between the first and second inclined outer surfaces of the first and second specimen grips and the first and second internal surfaces of the grip shell, respectively, so as to abutting engage with the first and second specimen grips, respectively, and define a separate wedge-like interface between each of the specimen grips and the first and second inserts and, to each provide corresponding external contact surfaces for the grip shell; and a jacking mechanism, situated within a recess in the jaw housing, for applying a mechanical force between an interior surface of the jaw housing and a surface of the specimen grip assembly so as to fixedly secure the specimen grip assembly into position within the jaw housing;

wherein, once jacking mechanism is set to apply the force between the jaw housing and the specimen grip assembly, a subsequent tensile or compressive force applied through the jaw housing and the grip assembly and sufficient to deform the test specimen will not generate any appreciable and noticeable compliance in the first and second specimen grips.

18. The apparatus recited in claim 17 wherein the grip shell is a unitary piece of material.

19. The apparatus recited in claim 18 wherein the grip shell has a truncated frusto-pyramidal exterior shape with a vertical cross-sectional shape that is trapezoidal.

20. The apparatus recited in claim 19 wherein the grip shell has a horizontal cross-sectional shape that is rectilinear.

21. The apparatus recited in claim 19 wherein the grip shell further comprises:

first and second external sloping surfaces at opposing ends of the grip shell; and the jaw housing has first and second internal surfaces that are inclined at an angle complementary to the first and second external sloping surfaces, respectively, of the grip shell;

the first and second external sloping surfaces of the grip shell abuttingly mating with and sliding against the first and second internal inclined surfaces of the jaw housing such that a separate wedge-shaped interface is formed between the jaw housing and each end of the grip shell.

22. The apparatus recited in claim 19 wherein the first and second inserts comprise first and second inner inserts and first and second outer inserts, respectively, wherein:

the first and second inner inserts extend between the first and second surfaces of the first and second specimen grips and the first and second inclined surfaces of the grip shell, respectively, and abuttingly engage with the first and second specimen grips, respectively, so as to form a wedge-like interface between one of the specimen grips and a corresponding one of the inner inserts; and the first and second outer inserts extend between the first and second inner inserts and the first and second external surfaces of the grip shell so as to abuttingly engage with the first and second inner inserts, respectively, and each one of the outer inserts provides the corresponding external contact surface for the grip shell.

* * * * *